(12) United States Patent
Young et al.

(10) Patent No.: US 11,502,847 B2
(45) Date of Patent: Nov. 15, 2022

(54) TECHNIQUES FOR MANAGING ANALYTICAL INFORMATION USING DISTRIBUTED LEDGER TECHNOLOGY

(71) Applicant: WATERS TECHNOLOGIES IRELAND LIMITED, Dublin (IE)

(72) Inventors: Phillip Young, Cheshire (GB); Richard Chapman, Cheshire (GB); Simon Meffan-Main, Manchester (GB)

(73) Assignee: WATERS TECHNOLOGIES IRELAND LIMITED, Dublin (IE)

( * ) Notice: Subject to any disclaimer, the term of this patent is extended or adjusted under 35 U.S.C. 154(b) by 512 days.

(21) Appl. No.: 16/510,139

(22) Filed: Jul. 12, 2019

(65) Prior Publication Data

US 2020/0021444 A1 Jan. 16, 2020

Related U.S. Application Data

(60) Provisional application No. 62/697,820, filed on Jul. 13, 2018.

(51) Int. Cl.
*G06F 21/00* (2013.01)
*H04L 9/32* (2006.01)
*G06F 16/182* (2019.01)

(52) U.S. Cl.
CPC .......... *H04L 9/3247* (2013.01); *G06F 16/182* (2019.01)

(58) Field of Classification Search
CPC ............................ H04L 9/3247; G06F 16/182
See application file for complete search history.

(56) References Cited

U.S. PATENT DOCUMENTS

| | | | | |
|---|---|---|---|---|
| 9,405,665 | B1* | 8/2016 | Shashi | G06F 11/3664 |
| 10,181,948 | B1* | 1/2019 | Nenov | G06F 8/65 |
| 10,658,076 | B2* | 5/2020 | Gulati | G16H 50/20 |
| 10,891,234 | B2* | 1/2021 | Noll | G06F 12/0864 |
| 11,036,777 | B2* | 6/2021 | Ono | G06F 16/9038 |
| 2009/0300170 | A1* | 12/2009 | Bhame | H04L 45/00 709/224 |
| 2012/0089344 | A1* | 4/2012 | Wright | G01N 30/8624 702/32 |
| 2015/0339218 | A1* | 11/2015 | Ekambaram | G06F 11/36 714/38.1 |

(Continued)

FOREIGN PATENT DOCUMENTS

EP 3340213 A1 6/2018

OTHER PUBLICATIONS

International Search Report and Written Opinion for International applicaiton No. PCT/IB2019/055979, dated Jun. 8, 2020, 17 pages.

(Continued)

*Primary Examiner* — Ghodrat Jamshidi
(74) *Attorney, Agent, or Firm* — Goodwin Procter LLP

(57) ABSTRACT

Techniques and apparatus for ion source devices with minimized post-column volumes are described. In one embodiment, for example, an apparatus may include at least one memory, and logic coupled to the at least one memory. The logic may be configured to receive analytical information from at least one analytical instrument, and generate at least one record in a distributed ledger having a transaction associated with at least a portion of the analytical information. Other embodiments are described.

22 Claims, 8 Drawing Sheets

(56) References Cited

U.S. PATENT DOCUMENTS

| | | | |
|---|---|---|---|
| 2016/0328945 A1* | 11/2016 | Greisser | F24F 11/30 |
| 2017/0017765 A1* | 1/2017 | Yegge | G16H 40/63 |
| 2017/0083860 A1 | 3/2017 | Sriram et al. | |
| 2018/0082043 A1 | 3/2018 | Witchey et al. | |
| 2018/0089644 A1* | 3/2018 | Chen | G06Q 20/24 |
| 2018/0218779 A1* | 8/2018 | Collins, Jr. | G16H 10/60 |
| 2018/0254093 A1* | 9/2018 | Rose | H04L 63/0478 |
| 2018/0284093 A1* | 10/2018 | Brown | H04W 4/35 |
| 2018/0368819 A1* | 12/2018 | Gogineni | A61B 5/6887 |
| 2019/0019570 A1* | 1/2019 | Fuertinger | G16H 50/70 |
| 2019/0220829 A1* | 7/2019 | Ripley | G06Q 10/30 |
| 2019/0253260 A1* | 8/2019 | Uehara | G09C 1/00 |
| 2019/0312855 A1* | 10/2019 | Sharma | G06F 16/1834 |
| 2020/0020038 A1* | 1/2020 | Haile | H04L 9/3236 |
| 2020/0356547 A1* | 11/2020 | Furukawa | H04L 9/3239 |

OTHER PUBLICATIONS

Caro, M.P., et al., "Blockchain-based Traceability in Agri-Food Supply Chain Management: A Practical Implementation", 2018 IoT Vertical and Topical Summit on Agriculture, IEEE (IOT Tuscany) (May 2018) 4 pages.

Ahram, T., et al., "Blockchain Technology Innovations" 2017 IEEE Technology and Engineering Management Conference (TEMSCON) (Jun. 2017) 5 pages.

\* cited by examiner

| Record ID 510 | User ID 512 | Timestamp 514 | Cryptography information 516 | Ownership 518 | Accreditation 520 | Signatures 522 | Data 524 |
|---|---|---|---|---|---|---|---|
| 0001 | ABC | 01-01-12:00 | Hash: hash_01<br>Previous: nil | ABC | FDA | Sig_01 | |
| 0002 | DEF | 01-01-12:35 | Hash: hash_02<br>Previous: 01 | DEF<br>GHI | N/A | N/A | Transaction_01 |
| ... | ... | ... | ... | ... | ... | ... | ... |
| n | XYZ | 02-01-12:00 | Hash: hash_n<br>Previous: n-1 | DEF<br>GHI | N/A | N/A | Transaction_N |

TECHNIQUES FOR MANAGING ANALYTICAL INFORMATION USING DISTRIBUTED LEDGER TECHNOLOGY

CROSS-REFERENCE TO RELATED APPLICATIONS

This application claims the benefit of and priority to U.S. Provisional Patent Application No. 62/697,820, filed on Jul. 13, 2018, the entire contents of which are incorporated by reference.

TECHNICAL FIELD

Embodiments herein generally relate to managing processes for analytical instruments, and, more particularly, to processes for generating distributed ledgers for managing data generated by analytical instruments.

BACKGROUND

Most industries are required to comply with various regulations in order to operate or provide goods within a certain jurisdiction. For example, pharmaceutical manufacturers are regulated by the U.S. Food and Drug Administration (FDA) within the United States, the Medicines and Healthcare Products Regulatory Agency (MHRA) in the United Kingdom, and the European Medicines Agency (EMA) within the European Union. Conventional compliance systems typically involve third party auditors examining information stored on paper and/or in centralized databases that require individualized access. The information may include an audit trail intended to demonstrate that the manufacturer followed regulatory protocols and/or a chain of custody indicating control and sources of component products. Analytical information may be used as part of a compliance routine, for instance, to demonstrate the components of a product or to ensure purity standards. For example, chromatography and/or mass analysis data (e.g., mass spectrometry data) may be used to ensure the chemical makeup of a pharmaceutical component.

Conventional compliance systems are highly susceptible to data integrity issues. For instance, data may be manipulated either intentionally or unintentionally and/or may otherwise become inconsistent in the supply chain. Manufacturers and auditors may be required to expend a large amount of resources and time to determine the source for such data integrity issues, which may not be able to be resolved using existing systems. Accordingly, conventional compliance systems are inefficient and vulnerable to manipulation, leading to a lack of trust in certain industrial sectors and unnecessary expenditure of time and resources.

SUMMARY

In accordance with various aspects of the described embodiments is an apparatus, the apparatus including at least one memory and logic coupled to the at least one memory, the logic operative to receive analytical information from at least one analytical instrument, and generate at least one record in a distributed ledger having a transaction associated with at least a portion of the analytical information. In some embodiments, the at least one analytical instrument may include at least one of a chromatography system or a mass analysis system. In some embodiments, the at least one analytical instrument may include at least one of a liquid chromatography (LC) system, a gas chromatography (GC) system, a mass analyzer system, a mass spectrometer (MS) system, an ion mobility spectrometer (IMS) system, a high-performance liquid chromatography (HPLC) system, a ultra-performance liquid chromatography (UPLC®) system, an ultra-high performance liquid chromatography (UHPLC) system.

In various embodiments, the at least one analytical information may include at least one of analysis information or operating information. In exemplary embodiments, the analytical information may include analysis information, the analysis information comprising data acquired or generated by an analytical instrument such as a spectrum or a chromatogram. In exemplary embodiments, the analytical information may include operating information for the analytical instrument, the operating information comprising at least one an operating log, an audit trail, or a digital signature. In various embodiments, the distributed ledger may be stored on a computing device communicatively coupled to the apparatus. In some embodiments, the logic may operate to store a shared copy of the distributed ledger in the at least one memory.

In exemplary embodiments, the logic may determine compliance with a regulatory protocol based on at least one record of the distributed ledger. In various embodiments, the logic may generate the record as part of an audit trail based on the analytical information within the distributed ledger. In some embodiments, the logic may generate the record as part of a chain of custody based on the analytical information within the distributed ledger. In various embodiments, the logic may implement a smart contract based on the analytical information via at least one record of the distributed ledger. In some embodiments, the logic may verify at least a portion of the analytical information. In various embodiments, the logic may generate the record in the distributed ledger responsive to a failure to verify the at least a portion of the analytical information. In exemplary embodiments, the distributed ledger may include a blockchain distributed ledger.

In exemplary embodiments, distinct elements of multiple distributed ledgers may be retrieved and compared to determine compliance with a regulatory protocol.

In accordance with various aspects of the described embodiments is a computer-implemented method that may include, by a processor, receiving analytical information from at least one analytical instrument, and generating at least one record in a distributed ledger having a transaction associated with at least a portion of the analytical information.

In some embodiments, the at least one analytical instrument may include at least one of a chromatography system or a mass analysis system. In various embodiments, the at least one analytical instrument may include at least one of a liquid chromatography (LC) system, a gas chromatography (GC) system, a mass analyzer system, a mass spectrometer (MS) system, an ion mobility spectrometer (IMS) system, a high-performance liquid chromatography (HPLC) system, a ultra-performance liquid chromatography (UPLC®) system, an ultra-high performance liquid chromatography (UHPLC) system.

In some embodiments, the at least one analytical information may include at least one of analysis information and operating information. In exemplary embodiments, the analytical information may include analysis information, the analysis information comprising at least one of a spectrum or a chromatogram. In some embodiments, the analytical information may include operating information for the analytical instrument, the operating information may include at least one of an operating log, an audit trail, or a digital signature.

In various embodiments, the method may include determining compliance with a regulatory protocol based on at least one record of the distributed ledger. In some embodiments, the method may include generating the record as part of an audit trail based on the analytical information within the distributed ledger. In exemplary embodiments, the method may include generating the record as part of a chain of custody based on the analytical information within the distributed ledger. In various embodiments, the method may include implementing a smart contract based on the analytical information via at least one record of the distributed ledger. In some embodiments, the method may include verifying at least a portion of the analytical information. In exemplary embodiments, the method may include generating the record in the distributed ledger responsive to a failure to verify the at least a portion of the analytical information. In various embodiments, the distributed ledger may include a blockchain distributed ledger.

In accordance with various aspects of the described embodiments is an analytical exchange system that may include at least one computing device that includes logic to implement an analytical exchange platform, the logic to provide a distributed ledger, receive analytical information from at least one producer node for at least one analytical instrument, generate at least one record in the distributed ledger having a transaction associated with at least a portion of the analytical information, and provide access to the distributed ledger to at least one consumer node.

In some embodiments, the at least one analytical instrument may include at least one of a chromatography system or a mass analysis system. In various embodiments, the at least one analytical instrument may include at least one of a liquid chromatography (LC) system, a gas chromatography (GC) system, a mass analyzer system, a mass spectrometer (MS) system, an ion mobility spectrometer (IMS) system, a high-performance liquid chromatography (HPLC) system, an ultra-performance liquid chromatography (UPLC®) system, or an ultra-high performance liquid chromatography (UHPLC) system.

In some embodiments, the analytical information may include analysis information, the analysis information comprising at least one of a spectrum or a chromatogram. In some embodiments, the analytical information may include operating information for the analytical instrument, the operating information comprising at least one an operating log, an audit trail, or a digital signature. In various embodiments, the logic may push a copy of a shared distributed ledger to that at least one consumer node. In some embodiments, the logic may ensure a secure and/or authenticated connection from the analytical instrument to the distributed ledger to create the at least one record.

In some embodiments, the logic may determine compliance with a regulatory protocol based on at least one record of the distributed ledger. In various embodiments, the logic may generate the record as part of an audit trail based on the analytical information within the distributed ledger. In some embodiments, the logic may generate the record as part of a chain of custody based on the analytical information within the distributed ledger. In exemplary embodiments, the distributed ledger may include a blockchain distributed ledger.

BRIEF DESCRIPTION OF THE DRAWINGS

FIG. 5 depicts a distributed ledger according to some embodiments.

DETAILED DESCRIPTION

Figure 1:
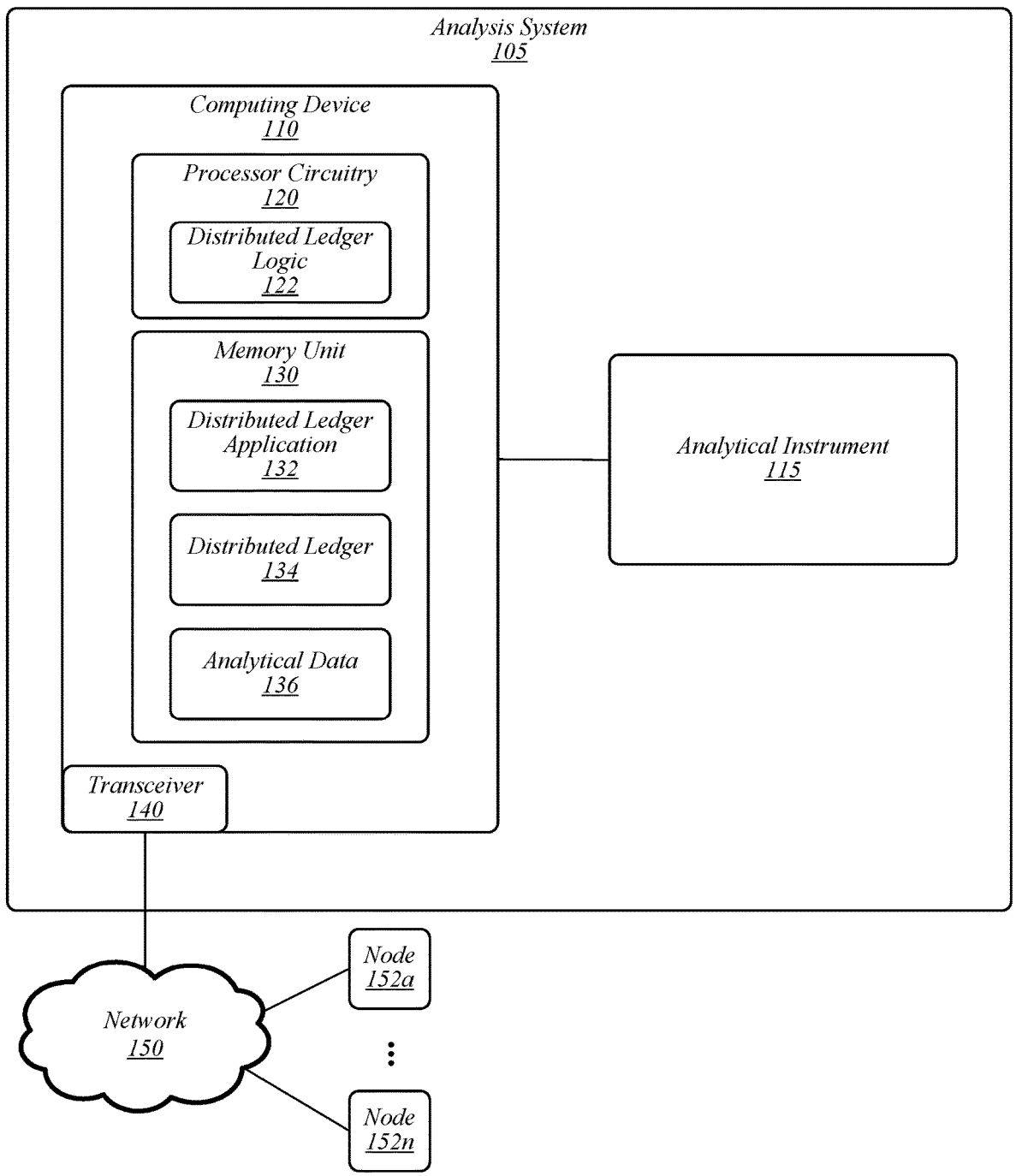
FIG. 1 illustrates an embodiment of a first operating environment.

Various embodiments may generally be directed toward systems, methods, and/or apparatus for managing analytical information using distributed ledger technology. In some embodiments, analytical information generated by an analytical instrument may be incorporated into a distributed ledger. For example, an analytical instrument may include a mass spectrometer operative to generate spectra resulting from mass analysis of a compound. During the analysis, the mass spectrometer may generate operating information associated with the operation of the mass spectrometer, such as quality control test results (for instance, spectra for blanks, solvents, and/or the like), digital signatures associated with operation of the mass spectrometer, timestamp information, sample source information (for instance, chain of custody information associated with the sample), and/or the like. The analytical information for the mass spectrometer may include the spectra (for instance, the analysis results) and the operating information (for instance, information relating to the operation of the instrument when generating the analysis results). In some embodiments, the analytical information may be generated as a marker, signature, identifier, tag, fingerprint, or other identifying characteristic of a component, such as a chemical compound, food product, material, and/or the like. In various embodiments, the analytical information may be stored in a distributed ledger, for example, as one or more transactions or blocks. For example, the analytical information may be or may include a unique fingerprint of a component within the distributed ledger that operates to identify the component and/or characteristics thereof.

In some embodiments, an analytical information exchange platform may operate to provide access to analytical information stored in a distributed ledger. The distributed ledger may be stored on one or more computing devices within a network. A plurality of entities may have access to read and/or write to the distributed ledger, for example, through the analytical information exchange platform. Such entities may access the distributed ledger via a secured or authenticated connection, with details of the entity accessing or modifying the distributed ledger being stored in the one or more transactions or blocks (for example, information relating to the identity, role, or location of the entity, a unique identifier for the entity, the date or time that the transaction or block is created by the entity). For example, a supplier of a product component may store analytical information associated with the component in the distributed ledger. A manufacturer obtaining the component from the supplier may be able to access the analytical information within the distributed ledger through the analytical information exchange platform, for example, to determine if it meets regulatory protocols prior to using the component to manufacture a pharmaceutical. In addition, a regulator (for instance, the U.S. Food and Drug Administration (FDA)) may also access the analytical information associated with the component within the distributed ledger through the analytical information exchange platform, for example, as part of an audit. Although pharmaceutical industry entities may be used in certain examples herein, embodiments are not so limited, as embodiments may operate with other types of entities, industries, research, analytics, and/or the like, including, without limitation, healthcare entities, biomedical entities, chemical entities, certification entities (for instance, organic certification, fair trade certification, source certification, and/or the like), food suppliers, material suppliers, product manufacturers, and/or the like.

In general, a distributed ledger is a record of consensus with a cryptographic audit trail which is maintained and validated by a plurality of computing nodes. For example, a distributed ledger may be implemented as a database that is shared, replicated, and synchronized among the computing nodes of a decentralized network. The distributed ledger records transactions, such as data, asset exchanges, and/or the like. Distributed ledgers can be decentralized, granting equal rights within the protocol to all participants or centralized, designating certain users' particular rights. The state of a distributed ledger may be determined through a consensus algorithm operative to validate information from inputs to the network. A blockchain is a particular implementation of a distributed ledger that includes a shared, replicated ledger that is formed of unchangeable data in packages called blocks. A blockchain sits below a distributed ledger and acts as a way to order and validate the transactions in the ledger. Non-limiting examples of distributed ledgers (or blockchain implementations thereof) may include Bitcoin, Ethereum, ERIS, Tendermint, Hyperledger, Axoni, Chain, R3, itBit, Clearmatics, Blockstack, Factom, Open Assets, Tierion, combinations thereof, variations thereof, and/or the like.

Various implementations of a distributed ledger may include characteristics including, without limitation, a ledger, consensus, cryptography, provenance, and immutability. The ledger may include a shared, permissioned ledger which may operate as an append-only system of record in which new records may only be appended to the ledger and existing records cannot be deleted or modified. All participants within a network may have their own identical copy of the ledger and any changes to the ledger are reflected in all copies. Consensus is required to add information to the ledger. For example, in order for a new record or block to be created or a transaction to be written to an existing block, the record must be validated by a consensus algorithm. In general, a consensus protocol agreed to by participating members ensures that the ledger is updated only with network-verified transactions and, as a result, that all participants (or a threshold number of participants) agree on the network's validity. Non-limiting examples of consensus algorithms may include proof-of-work, Byzantine fault-tolerant replication, proof-of-stake, multi-signature, and/or the like.

Distributed ledgers use cryptography to maintain a peer-to-peer distributed, time-stamped and immutable consensus ledger of all past transactions. Each transaction (or record of a transaction) is similar to a ledger line item, which is then aggregated with others into a block of records or transactions, essentially forming a chain of records (or blocks for a blockchain implementation), with each record connected to the previous record. For example, a distributed ledger involves a chain of cryptographic hashes in which each record contains a cryptographic hash to the previous record. The cryptographic hash may provide assurance as to the integrity of a record, for instance as a checksum, because any change to the contents of the record will result in a completely different cryptographic hash being produced. With each record referring back to the previous record, it is not possible to insert a new block or alter an existing record's contents, thus providing a range of guarantees as to the integrity of the order and contents of the records.

The provenance of a distributed ledger may generally refer to sources/processes that produce information/data. In cryptography, provenance may provide the linkage and other information to determine a source of information and/or a record. As such, distributed ledger technology can be used to determine the provenance of an asset or information, which may determine a source and/or a history of ownership of the asset or information. In addition, distributed ledgers may demonstrate immutability because network participants cannot tamper with transactions once they are recorded in the distributed ledger. For example, if a record or transaction is the result of an error, another record or transaction must be added to correct the error and both transactions (the original, erroneous record, and the corrected record) must be left visible to the network participants.

Distributed ledger technology may be used to implement smart contracts, which may include programmable contracts capable of automatically enforcing themselves when pre-defined conditions have been met. For example, a smart contract may include the terms of a contract between at least two entities. The smart contract operates to monitor information and/or events to trigger the pre-defined conditions. When the pre-defined conditions are met, the contract is executed and the smart contract may provide data for compliance and reporting (for instance, as a record within the distributed ledger). A non-limiting example of a smart contract may include a program operative to indicate that a product component is available to be shipped responsive to passage of a quality control test by the supplier, or to passage of a verification check to confirm that data associated with the product component either matches or is determined to be substantially similar to data associated with validated or authentic product components or to data received in a prior transaction or block in the distributed ledger. Such substantial similarity may be calculated by any of a number of known techniques, including, without limitation, through reference to a statistical model (for example, a model built through analysis of validated or authentic samples by either supervised or unsupervised learning algorithms such as principal component analysis (PCA) and/or linear discriminant analysis (LDA)), reference to permissible modifications known to occur to a particular product component over time (for example, degradation to a particular food product as a function of time), reference to permissible variations to the product component that do not violate the terms of the smart contract (for example, a quality control measurement value that continues to fall within a permissible range), and/or the like. Embodiments are not limited in this context.

In this description, numerous specific details, such as component and system configurations, may be set forth in order to provide a more thorough understanding of the described embodiments. It will be appreciated, however, by one skilled in the art, that the described embodiments may be practiced without such specific details. Additionally, some well-known structures, elements, and other features have not been shown in detail, to avoid unnecessarily obscuring the described embodiments.

In the following description, references to "one embodiment," "an embodiment," "example embodiment," "various embodiments," etc., indicate that the embodiment(s) of the technology so described may include particular features, structures, or characteristics, but more than one embodiment may and not every embodiment necessarily does include the particular features, structures, or characteristics. Further, some embodiments may have some, all, or none of the features described for other embodiments.

As used in this description and the claims and unless otherwise specified, the use of the ordinal adjectives "first," "second," "third," etc. to describe an element merely indicate that a particular instance of an element or different instances of like elements are being referred to, and is not intended to imply that the elements so described must be in a particular sequence, either temporally, spatially, in ranking, or in any other manner.

FIG. 1 illustrates an example of an operating environment 100 that may be representative of some embodiments. As shown in FIG. 1, operating environment 100 may include an analysis system 105 operative to manage analytical information associated with analytical instrument 115. In some embodiments, analytical instrument 115 may be or may include a chromatography system, a liquid chromatography (LC) system, a gas chromatography (GC) system, a mass analyzer system, a mass detector system, a mass spectrometer (MS) system, an ion mobility spectrometer (IMS) system, a high-performance liquid chromatography (HPLC) system, a ultra-performance liquid chromatography (UPLC®) system, a ultra-high performance liquid chromatography (UHPLC) system, a solid-phase extraction system, a sample preparation system, a capillary electrophoresis instrument, combinations thereof, components thereof, variations thereof, and/or the like. Although LC, MS, and LC-MS are used in examples in this detailed description, embodiments are not so limited, as other analytical instruments capable of operating according to some embodiments are contemplated herein.

In some embodiments, analytical instrument 115 may operate to perform an analysis. For example, for an LC-MS system, analytical instrument 115 may separate a sample and perform mass analysis on the separated sample to generate analytical information 136. In some embodiments, analytical information 136 may include analysis information and/or operating information associated with the analytical instrument. In exemplary embodiments, analysis information may include information generated as the result of an analysis performed by analytical instrument 115, such as values, graphs, images, calculations, and/or the like. For example, for an LC system, analysis information may include a chromatogram. In another example, for an MS system, analysis information may include spectra. In various embodiments, operating information may include information associated with operation of analytical instrument 115 before, during, and/or after an analysis. For example, operating information may include digital signatures (for instance, of operators performing functions on analytical instrument 115), quality control test results, component information (for instance, voltages, pressures, flow rates, volumes, temperatures, error conditions, of analytical instrument 115 and/or components thereof, such as pumps, valves, columns, and/or the like), operating methods, regulatory protocols, audit trail information, environmental information, operating log information, sample source, and/or the like.

In some embodiments, the operating information may be generated for the analytical instrument 115 or components thereof, such as for a sample supply, an LC system, and/or an MS system of an LC-MS analytical instrument 115. In various embodiments, the operating information may be generated for each project, sample, run, or other quantifiable operation or function of analytical instrument. Non-limiting examples of audit trail information may include operators, digital signatures, analysis methods, completed method steps, operating parameters, operating conditions, batch, tuning, instrument resolutions, hardware/software profiles, security, system access, calibration, quality control, executed modules, changes to any of the foregoing (for instance, changes in analytical methods, changes in users, etc.), network connection status, analytical instrument-computing device connection status, maintenance protocols, instrument maintenance, power status (for instance, when the analytical instrument 115 is powered on or off), and/or the like.

In various embodiments, analysis system 105 may include computing device 110 communicatively coupled to analytical instrument 115 or otherwise configured to receive and store analytical information 136 associated with analytical instrument 115. For example, analytical instrument 115 may operate to provide analytical information to a location on a network 150 (for instance, a cloud computing environment) accessible to computing device 110. In some embodiments, computing device 110 may be operative to control, monitor, manage, or otherwise process various operational functions of analytical instrument 115. In some embodiments, computing device 110 may be operative to provide analytical information to a location on a network 150 through a secure or authenticated connection. In some embodiments, upon generation of the analytical information by the analytical instrument 115, the computing device 100 or analytical instrument 115 may be operative to automatically transfer the analytical information to a location on network 150. In some embodiments, computing device 110 may be or may include a stand-alone computing device, such as a personal computer (PC), server, tablet computing device, cloud computing device, and/or the like.

As shown in FIG. 1, computing device 110 may include processing circuitry 120, a memory unit 130, and a transceiver 140. Processing circuitry 120 may be communicatively coupled to memory unit 130 and/or transceiver 140.

Processing circuitry 120 may include and/or may access various logic for performing processes according to some embodiments. For instance, processing circuitry 120 may include and/or may access distributed ledger logic 122. In general, distributed ledger logic 122 can be circuitry arranged to perform specific operations related to processing a distributed ledger, such as, for example, encoding, decoding, encrypting, decrypting, validating, or the like. Processing circuitry and/or distributed ledger logic 122, or portions thereof, may be implemented in hardware, software, or a combination thereof. As used in this application, the terms "logic, "component," "layer," "system," "circuitry," "decoder," "encoder," and/or "module" are intended to refer to a computer-related entity, either hardware, a combination of hardware and software, software, or software in execution, examples of which are provided by the exemplary computing architecture 700. For example, a logic, circuitry, or a layer may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, combinations of any of the foregoing, and/or the like.

Although distributed ledger logic 122 is depicted in FIG. 1 as being within processing circuitry 120, embodiments are not so limited. For example, distributed ledger logic 122 may be located within an accelerator, a processor core, an interface, an individual processor die, implemented entirely as a software application (for instance, distributed ledger application 132) and/or the like.

Memory unit 130 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In addition, memory unit 130 may include various types of computer-readable storage media in the form of one or more lower speed memory units, including an internal (or external) hard disk drive (HDD), a magnetic floppy disk drive (FDD), and an optical disk drive to read from or write to a removable optical disk (e.g., a CD-ROM or DVD), a solid state drive (SSD), and/or the like.

Memory unit 130 may store a distributed ledger application 132 that may operate, alone or in combination with distributed ledger logic 122, to perform various distributed ledger functions according to some embodiments. For example, distributed ledger application 132 may maintain a distributed ledger 134 stored locally in memory unit 130 and/or on a node 152a-n of network 150. In various embodiments, distributed ledger application 132 may generate records in distributed ledger 134 for analytical information 136 generated by analytical instrument 115. For example, distributed ledger application 132 may generate one or more records for each corresponding event recorded in an audit trail or other log associated with operation of an analytical instrument. In another example, distributed ledger application 132 may generate one or more records for each analysis result generated by an analytical instrument. In another example, distributed ledger application 132 may retrieve one or more records from one or more distributed ledgers 134 accessible by the distributed ledger application 132, such as records created within a designated time range, records created or that contain data created by a particular analytical instrument, records created by a particular entity, and/or the like.

In some embodiments, distributed ledger application 132 include application programming interfaces (APIs) to provide access to distributed ledger 134, such as through graphical user interfaces (GUIs), web interfaces, mobile application ("mobile applications," "mobile apps," or "apps"), and/or the like. In this manner, an operator may search, visualize, read, add to, or otherwise access records of distributed ledger 134. However, in various embodiments, an operator may not change or delete records in distributed ledger 134.

In various embodiments, distributed ledger application 132 may operate to implement or facilitate a chain of custody, compliance, and/or audit trail process. For example, analytical instrument 115 may be required to provide analytical information 136 to distributed ledger application 132, which may generate a record (or block) in distributed ledger 134 for one or more items of analytical information 136. In this manner, the entirety of the operation of analytical instrument 115 may be recorded in distributed ledger 134 for access by interested parties (for example, a vendor, a customer, a parent company, a contractor, a regulatory body). Accordingly, the integrity of data generated by analytical instrument 115 and the operation of analytical instrument 115 may be examined through distributed ledger 134 with the benefits of a distributed ledger technology (for instance, immutability, consensus, and/or the like).

In some embodiments, the analytical information 136 may be or may include an identifier, "tag", or "fingerprint" for a component, such as a chemical compound, material, food product, and/or the like. For example, a chemical compound may be analyzed by analytical instrument 115 to generate analysis information (for instance, spectra, components (for instance, chemical composition), component ratios, and/or the like) that may be included as a unique chemical (or molecular) fingerprint for the chemical compound and stored in a record in distributed ledger 134. In another example, a doping agent with a potentially unique chemical (or molecular) fingerprint may be included with or added to a substance being analyzed by analytical instrument 115 in order to "tag" the substance for later verification and/or validation, such as by subsequent analysis by analytical instrument 115. Analysis information of the compound with the doping agent may be retained in distributed ledger 134. The presence or absence of the anticipated "tag" in analysis information obtained in subsequent analyses may indicate whether the chain of custody for the substance has been maintained. In another example, a food product may be analyzed by analytical instrument 115 to determine analysis information that may include nucleic acid information (for instance, DNA), protein information, and/or the like. The analysis information for the food product may be used as a unique genetic fingerprint, which may be included in distributed ledger 134. In this manner, the "fingerprints" associated with a physical product may be generated as verified and verifiable information that may be linked to the physical product. A physical product may be linked to a digital asset and/or information, such as distributed ledger 134 and/or records thereof.

Accordingly, in some embodiments, assertions about a component or product (for instance, source, purity, organic, fair trade, composition, and/or the like) may be linked to verified information (for instance, a fingerprint) and included in distributed ledger 134. For example, a product may be fingerprinted or tagged at an origin (or other point in a supply chain) and the fingerprint or tag may be accessed, viewed, detected, verified, or otherwise analyzed at a later point in the chain. In some embodiments, a product may be associated with a plurality of fingerprints. For example, for a food product supply chain, a grower may generate a source fingerprint (for instance, location information generated by a device based on GPS information and/or an on-site device that generates unique location information, timestamp information, and/or the like) and a composition or genetic makeup fingerprint; a wholesaler of the food product may generate a food handling fingerprint (for instance, storage location and condition information, shipping information, and/or the like); a vendor may generate receipt information (for instance, timestamp information). Embodiments are not limited in this context.

In some embodiments, an operating condition of analytical instrument 115 is that it is connected to computing device 110 (or distributed ledger 134 is otherwise capable of storing analytical information 136 associated with analytical instrument). In other embodiments, a record may be generated in distributed ledger 134 indicating that computing device 110 is not connected to analytical instrument (or distributed ledger 134 is otherwise not capable of storing analytical information 136 associated with analytical instrument). In various embodiments, a record may be generated in distributed ledger 134 responsive to a computing device (other than computing device 110) establishing a connection to analytical instrument. In exemplary embodiments, a record may be generated in distributed ledger 134 responsive to analytical information 136 (for example, electronic files that include analytical information 136) stored in computing device 110, analytical instrument 115, and/or other devices, being accessed, read, written to, deleted, or otherwise modified. In this manner, all or substantially all operations and analysis results associated with analytical instrument 115 may be recorded in distributed ledger 134. In addition, the ability to tamper with analytical instrument 115 and/or analytical information 136 associated therewith without knowledge of other entities may be substantially reduced if not completely eliminated.

In some embodiments, distributed ledger application 132 may include settings for enabling/disabling the recording of types of analytical information 136. For example, distributed ledger application 132 may provide a GUI for allowing an operator to specify recordable events (for instance, analysis results, error conditions, digital signatures, and/or the like) and non-recordable events (for instance, solvent batch information, operator names, and/or the like). In various embodiments, distributed ledger application 132 may including settings for notifications associated with analytical information, such as alarms, messages, and/or the like responsive to certain analytical information 136 (for instance, error conditions, completion of an analysis method, loss of network connection, entity access, and/or the like).

In various embodiments, distributed ledger application 132 may operate to implement or facilitate verification of analytical information 136. For example, distributed ledger application 132 may have access to historical information, process information (for instance, standard protocols or method steps), and/or the like. Distributed ledger application 132 may operate to compare the audit trail or other log associated with an analysis, calibration, or other process being performed by analytical instrument 115 to determine whether the process is consistent with expected historical or process information. In some embodiments, if distributed ledger application 132 determines that a process is not consistent with historical or process information, distributed ledger application 132 may generate a record in distributed ledger 134 and/or generate an alert. In another example, distributed ledger application 132 may compare analysis results (for instance a spectrum for a compound) with historical information (for example, expected spectra for the compound) to determine if the analysis results match (for instance, within threshold tolerances) the expected results. In exemplary embodiments, if distributed ledger application 132 determines that analysis results are not consistent with expected results, distributed ledger application 132 may generate a record in distributed ledger 134 and/or generate an alert In various embodiments, distributed ledger application 132 may operate to implement or otherwise facilitate smart contracts associated with distributed ledger 134. In some embodiments, distributed ledger 134 may include a smart contract operative to trigger a contract event responsive to a triggering condition. In various embodiments, the triggering condition may be determined based on analytical information 136. For example, the triggering condition may include analytical instrument 115 passing a quality control or calibration routine, generating analysis information (for instance, a mass spectrum for a compound), analysis information matching or substantially similar to historical information (for instance, within tolerance thresholds), a digital signature (for instance, an operator with sufficient authority has digitally signed analysis information, an analysis method, and/or the like), combinations thereof. In some embodiments, the contract event may include any type of event agreed to between the parties, such as a release of an asset (for instance, monetary funds, a product, and/or the like), authorization to perform a function (for instance, ship a product, receive payment, and/or the like), regulatory approval, and/or the like. For example, a smart contract may include a contract event of regulatory approval by the FDA responsive to successful performance of a method, which may be indicated based on analytical information 115 and/or records in distributed ledger 134. In another example, a smart contract may include a contract event of approval for payment from a manufacturer to a supplier responsive to receipt of analytical information 115 (for instance, chromatogram, spectra, and/or the like) indicating that the product meets expected guidelines. Embodiments are not limited in this context.

Figure 2:
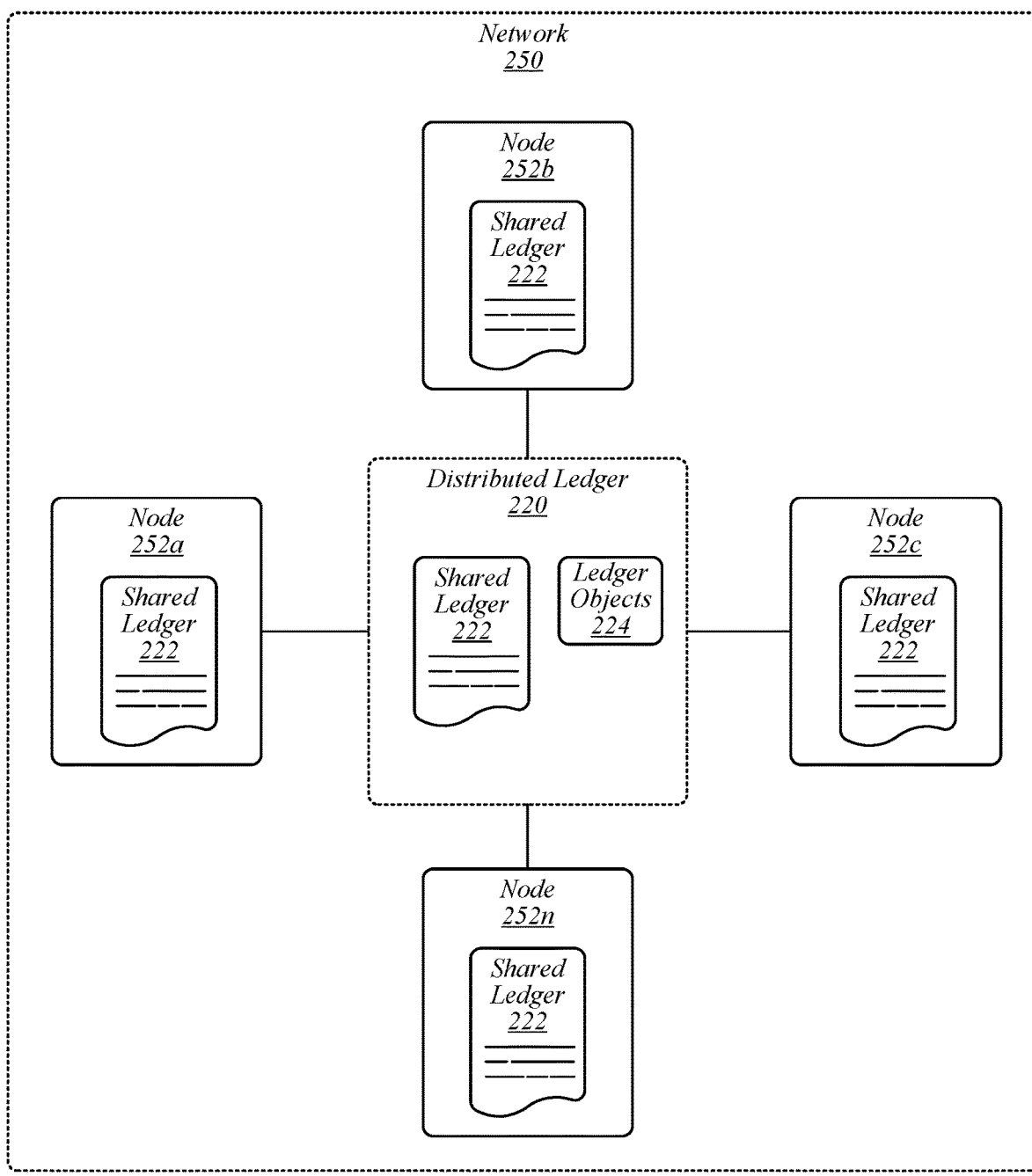
FIG. 2 illustrates an embodiment of a second operating environment.

FIG. 2 illustrates an example of an operating environment 200 that may be representative of some embodiments. As shown in FIG. 2, operating environment 200 may include a network 250 that includes nodes 252a-n and distributed ledger 220. In some embodiments, distributed ledger 220 may include shared ledger 222 and ledger objects 224 stored on one or more servers (not shown) of network 250. In some embodiments, ledger objects 224 may include smart contracts, APIs, and/or the like.

Each of nodes 252a-n may include a copy of shared ledger 222. One or more of nodes 252a-n may include various entities of interest to shared ledger 222. For example, shared ledger 222 may be operative as part of a regulatory process in which node 252a may be a compute node associated with a pharmaceutical manufacturer (for instance, that packages and cells a pharmaceutical), node 252b may be a compute node associated with a supplier to the pharmaceutical manufacturer (for instance, that makes a component of pharmaceutical or that makes the pharmaceutical for pharmaceutical manufacturer), node 252c may include a regulatory body, such as the FDA, and node 252n may include a purchaser of the pharmaceutical (for instance, a pharmacy chain, a hospital system, and/or the like). In another example, shared ledger 222 may be operative as part of a food supply chain in which node 252a may be a compute node associated with a food supplier (for instance, a fishery or crop producer), node 252b may be a compute node associated with a food distributor (for instance, a wholesaler that purchases a food product from an original supplier for sale to a vendor), and node 252c may be a compute node associated with a food certification authority (for instance, an entity that certifies the food product as being organic, fair trade, from a specific source/region, and/or the like). Additional entities may be included as a node 252*a-n* having access to distributed ledger 220.

In some embodiments, distributed ledger 220 may be permissioned or unpermissioned. In a permissioned embodiment, one or more owners manage control of and/or access to distributed ledger 220, such as rights to read, write, mine, and/or the like distributed ledger 220. In an unpermissioned embodiments, no single owner manages control of and/or access to distributed ledger 220, such that there is no central control of distributed ledger 220.

For example, in a permissioned implementation of distributed ledger 220, each entity may be provided differential access to distributed ledger 220 (and/or their individual copy of shared distributed ledger 222). For example, in an embodiment in which the pharmaceutical manufacturer (for example, as a client of a platform developer) is the owner, the pharmaceutical manufacturer may have full read/write access to distributed ledger 220, a supplier to pharmaceutical manufacturer may have full write access and partial read access (for instance, can only read records associated with its own activity), a regulator may have partial read/write access (for instance, can only read/write records associated with regulatory functions), and a purchaser may have partial read/write access (for instance, can only read/write records associated with purchases of specific compounds).

In some embodiments, distributed ledger 220 records may include a plurality of distributed ledgers associated with various elements. For example, for a pharmaceutical supply chain distributed ledger 220 for a pharmaceutical, distributed ledger 220 may include various distributed ledgers for each vendor, compound, regulatory process, pharmaceutical, purchaser, supplier, research organization, and/or the like. In such an embodiment, an owner of distributed ledger 220 may provide differential access to each of the plurality of distributed ledgers.

Figure 3:
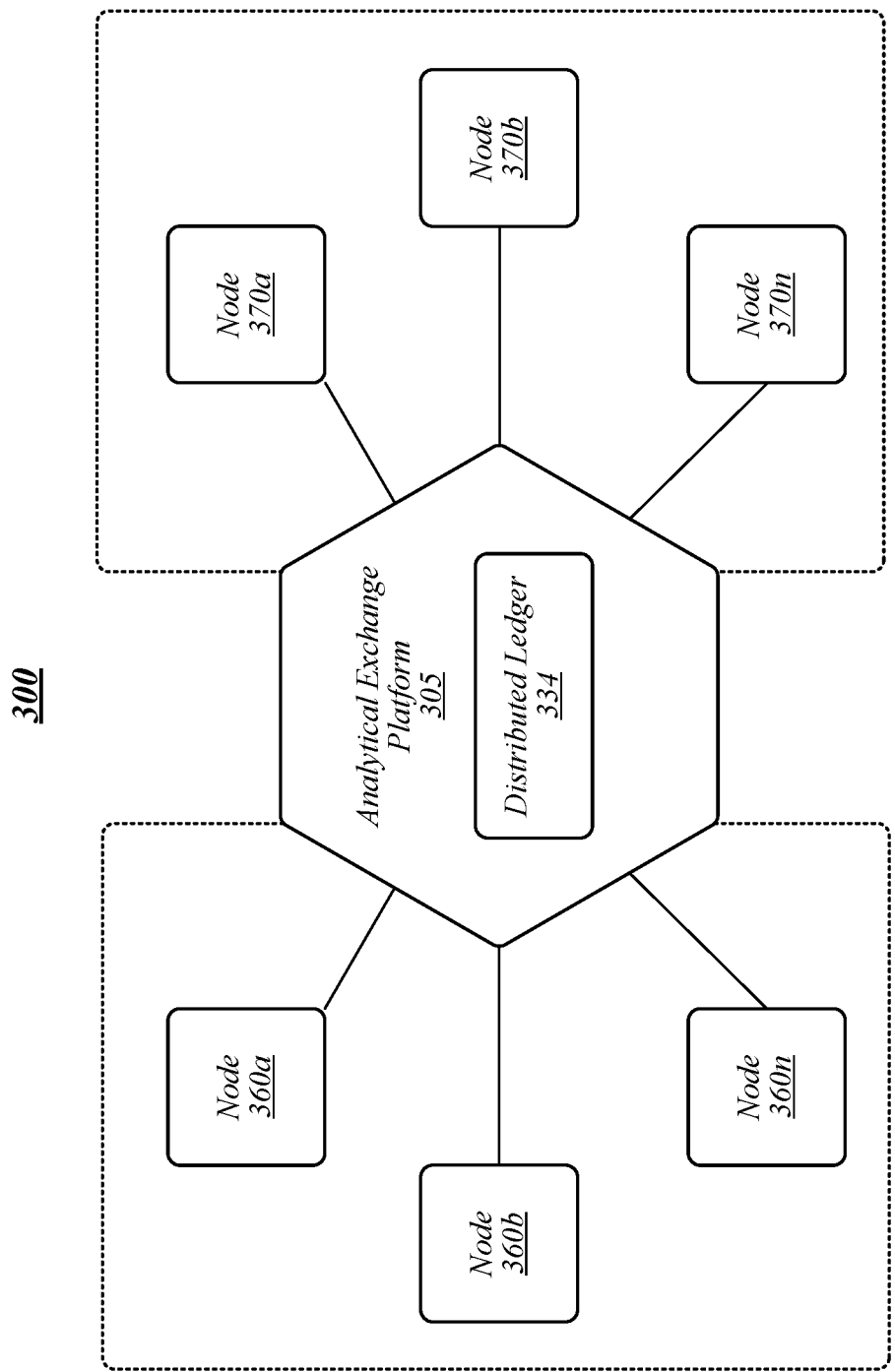
FIG. 3 illustrates an embodiment of a third operating environment.

FIG. 3 illustrates an example of an operating environment 300 that may be representative of some embodiments. As shown in FIG. 3, operating environment 300 may include an analytical exchange platform (or an analytical instrument platform) 305 associated with a distributed ledger 334. In some embodiments, analytical exchange platform 305 may be operative to provide for the exchange of analytical information among interested entities. In various embodiments, analytical exchange platform 305 may include an application platform operative to provide data exchange services among nodes 360*a-n* and 370*a-n*. In exemplary embodiments, analytical exchange platform 305 may be a software platform, suite, set of protocols, and/or the like provided to customers by a manufacturer, product source, and/or developer ("developer") associated with an analytical instrument. A non-limiting example of a developer may be the Waters Corporation of Milford, Mass., United States of America. For example, a developer may provide analytical exchange platform 305 as a data exchange interface for an LC, MS, LC-MS, and/or the like analytical instrument provided to an entity by the developer. An entity, such as a pharmaceutical manufacturer, research organization, product supplier, food supply chain entity, and/or the like using analytical instrument provided by developer may use analytical exchange platform 305 to implement distributed ledger 334 according to some embodiments. Other entities may access analytical exchange platform 305 via a GUI, such as a client application, web interface, mobile app, and/or the like, to perform functions associated with distributed ledger 334. In some embodiments, at least a portion of analytical exchange platform 305 may be hosted in a cloud computing environment.

Nodes 360*a-n* may be data producers for distributed ledger 334 and nodes 370*a-n* may be data consumers of distributed ledger 370*a-n*. For example, node 360*a-n* may include instruments, contract labs, and/or other data producers. Nodes 370*a-n* may include third-party applications, decision makers, analysis, regulators, and/or other data consumers. An entity may be both a data producer and a data consumer. For example, node 360*a* may be a research organization contracted by a pharmaceutical manufacturer (node 360*b*) to perform clinical trials on a compound to obtain regulatory approval by a regulator (node 370*a*). In another example, node 360*a* may be a food producer (or a contractor thereof) that performs analysis on its food products to generate a fingerprint for the food product as part of a supply chain for wholesaler (node 370*a*), to obtain certification from a certification authority (node 370*b*), and/or the like. Data producers 360*a-n* may provide analytical information, according to permissions, to analytical exchange platform 305, for example, in the form of records in distributed ledger. Data consumers 370*a-n* may access analytical information, according to permissions, via analytical exchange platform 305 (for example, through distributed ledger 334 and/or local copies of distributed ledger). In some embodiments, analytical exchange platform 305 may operate to ensure the consistency of local copies of distributed ledger 334, for instance, by pushing out updates to nodes 360*a-n* and/or 370*a-n*.

In some embodiments, analytical exchange platform 305 may operate according to a cloud-based model and/or an "as-a-Service" model. In this manner, analytical exchange platform 305 may provide for a service that provides a single, central platform that would allow entities to perform sample analysis alone with analysis chain of custody in which the entity could provide access to a partner of their choice. For example, a pharmaceutical manufacturer (node 370*a*) may provide access to analytical exchange platform 305 to a contract supplier (node 360*a*) to provide analytical information, such as chain of custody information, analysis information (for instance, spectra, and/or the like), regulatory compliance information, and/or the like via distributed ledger 334. In addition, pharmaceutical manufacturer may provide access to this information to a purchaser (node 370*b*) of a pharmaceutical via analytical exchange platform 305.

Figure 4:
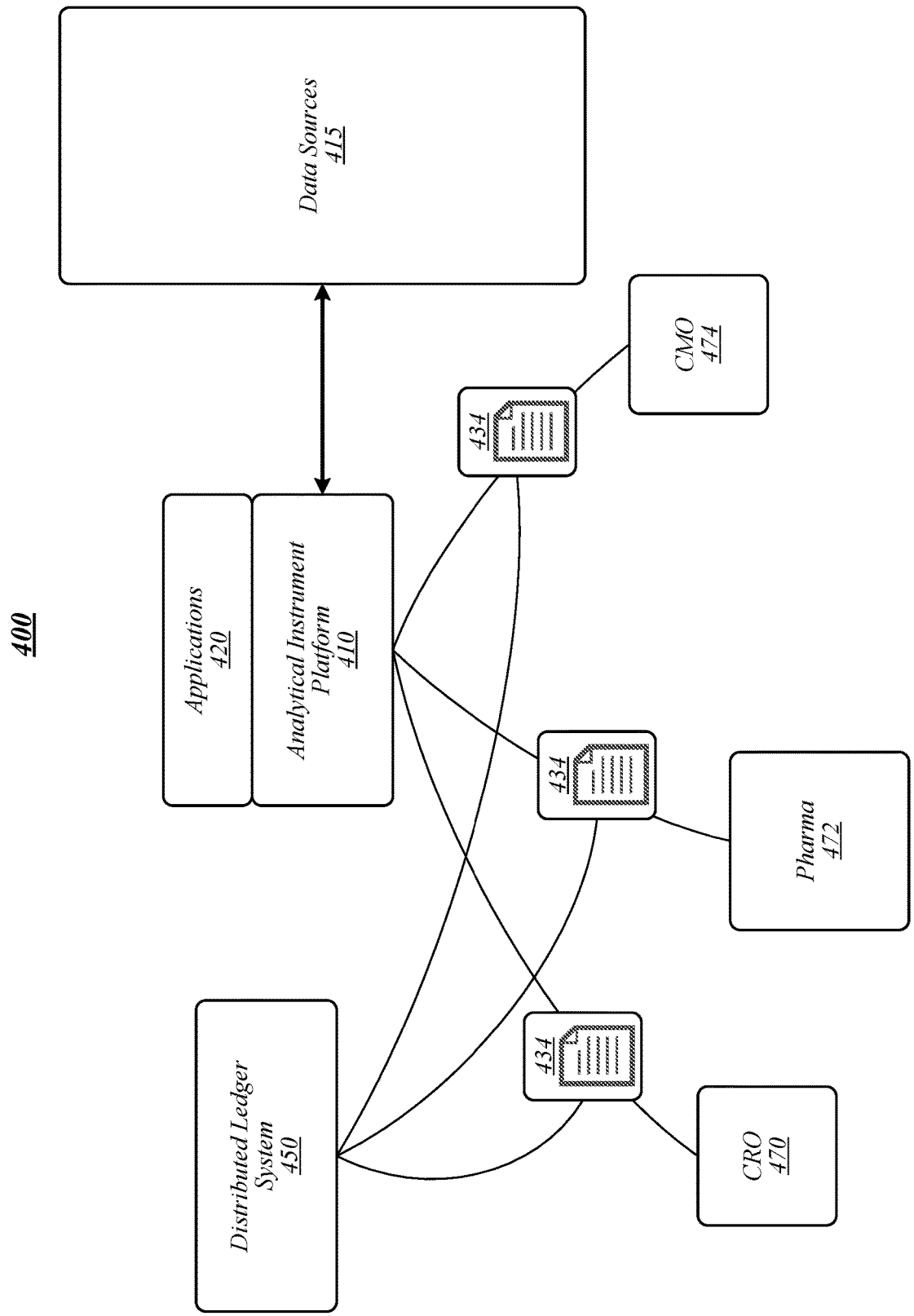
FIG. 4 illustrates an embodiment of a fourth operating environment.

FIG. 4 illustrates an example of an operating environment 400 that may be representative of some embodiments. As shown in FIG. 4, operating environment 400 may include an analytical instrument platform (or analytical exchange platform) 410 accessible by various entities, such as a pharmaceutical manufacturer 472 and a contract manufacturing organization (CMO) 474 and contract research organization (CRO) 470 contracted by pharmaceutical manufacturer 472. Analytical instrument platform 410 may implement, support, operate, or otherwise facilitate a distributed ledger system 450 according to some embodiments. Each of pharmaceutical manufacturer 472, CRO 470, and/or CMO 474 may have a shared ledger 434 based on distributed ledger system 450.

In some embodiments, analytical instrument platform 410 may receive information from one or more data sources 415, such as a laboratory information system (LIMS), an enterprise resource planning (ERP) system, a clinical information system (CIS), analytics information, visualization information, search information, and/or the like. The analytical instrument platform 410 may be associated with various applications 420 that may be associated with (for example, via APIs and/or the like) with analytical instrument platform 410. The applications 420 may be provided by a developer of analytical instrument platform 410 and/or third-party developers. In various embodiments, application 420 may provide additional functionality for analytical instrument platform 410, such as data visualization, search, and/or the like.

FIG. 5 depicts an illustrative distributed ledger 505 according to some embodiments. As shown in FIG. 5, distributed ledger 505 may include a database of records having various fields, such as a record ID 510 to uniquely identify the record, a user ID 512 to associate the user or entity associated with causing the record to be generated, and a timestamp 514 indicating when the record was created.

Each record may include cryptography information 516, for example, a unique hash and/or a pointer to the previous record. In this manner, if a record is changed or deleted, the cryptography information will not match and it may be determined that the distributed ledger 505 has been changed. In various embodiments, each record may include ownership information 518 indicating which entities have permission to read, write, and/or the like the record. Certain records may include accreditation information 520, such as what types of accreditation are associated with the record (for instance, FDA for pharmaceuticals, organic food entities for produce, and/or the like) and signature information 522 indicating any digital signatures associated with the record (for instance, a digital signature required for the associated transaction and/or to create the record). In some embodiments, each record may be associated with data 524, such as a data payload (for instance, analysis information, audit trail logs, operating logs, and/or the like) and/or transaction information (for example, indicating a transaction type and/or other transaction information).

Included herein are one or more logic flows representative of exemplary methodologies for performing novel aspects of the disclosed architecture. While, for purposes of simplicity of explanation, the one or more methodologies shown herein are shown and described as a series of acts, those skilled in the art will understand and appreciate that the methodologies are not limited by the order of acts. Some acts may, in accordance therewith, occur in a different order and/or concurrently with other acts from that shown and described herein. For example, those skilled in the art will understand and appreciate that a methodology could alternatively be represented as a series of interrelated states or events, such as in a state diagram. Moreover, not all acts illustrated in a methodology may be required for a novel implementation. Blocks designated with dotted lines may be optional blocks of a logic flow.

A logic flow may be implemented in software, firmware, hardware, or any combination thereof. In software and firmware embodiments, a logic flow may be implemented by executable computer instructions stored on a non-transitory computer readable medium or machine-readable medium, such as an optical, magnetic or semiconductor storage. The embodiments are not limited in this context.

Figure 6:
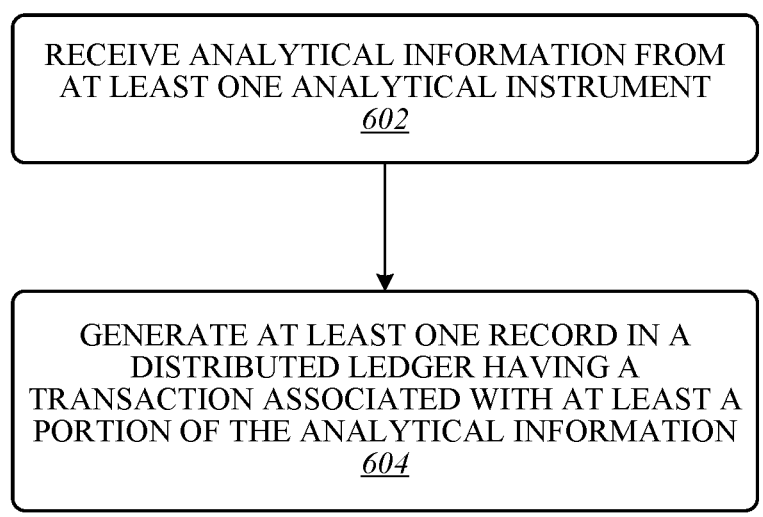
FIG. 6 illustrates an embodiment of a first logic flow.

FIG. 6 illustrates an embodiment of a logic flow 600. Logic flow 600 may be representative of some or all of the operations executed by one or more embodiments described herein, such as computing device 110, nodes 252a-n, nodes 360a-n, nodes 370a-n, and/or components of operating environment 400. In some embodiments, logic flow 600 may be representative of some or all of the operations of an enrollment process associated with an analytical services distributed ledger process according to some embodiments.

At block 602, logic flow 600 may receive analytical information from at least one analytical instrument. For example, analytical instrument 115 may provide analytical information 136 to distributed ledger application 132. Embodiments are not limited in this context.

Logic flow 600 may generate at least one record in a distributed ledger having a transaction associated with at least a portion of the analytical information at block 604. For example, distributed ledger application 132 may generate a record (or block) in distributed ledger 134 for one or more items of analytical information 136. Embodiments are not limited in this context.

Figure 7:
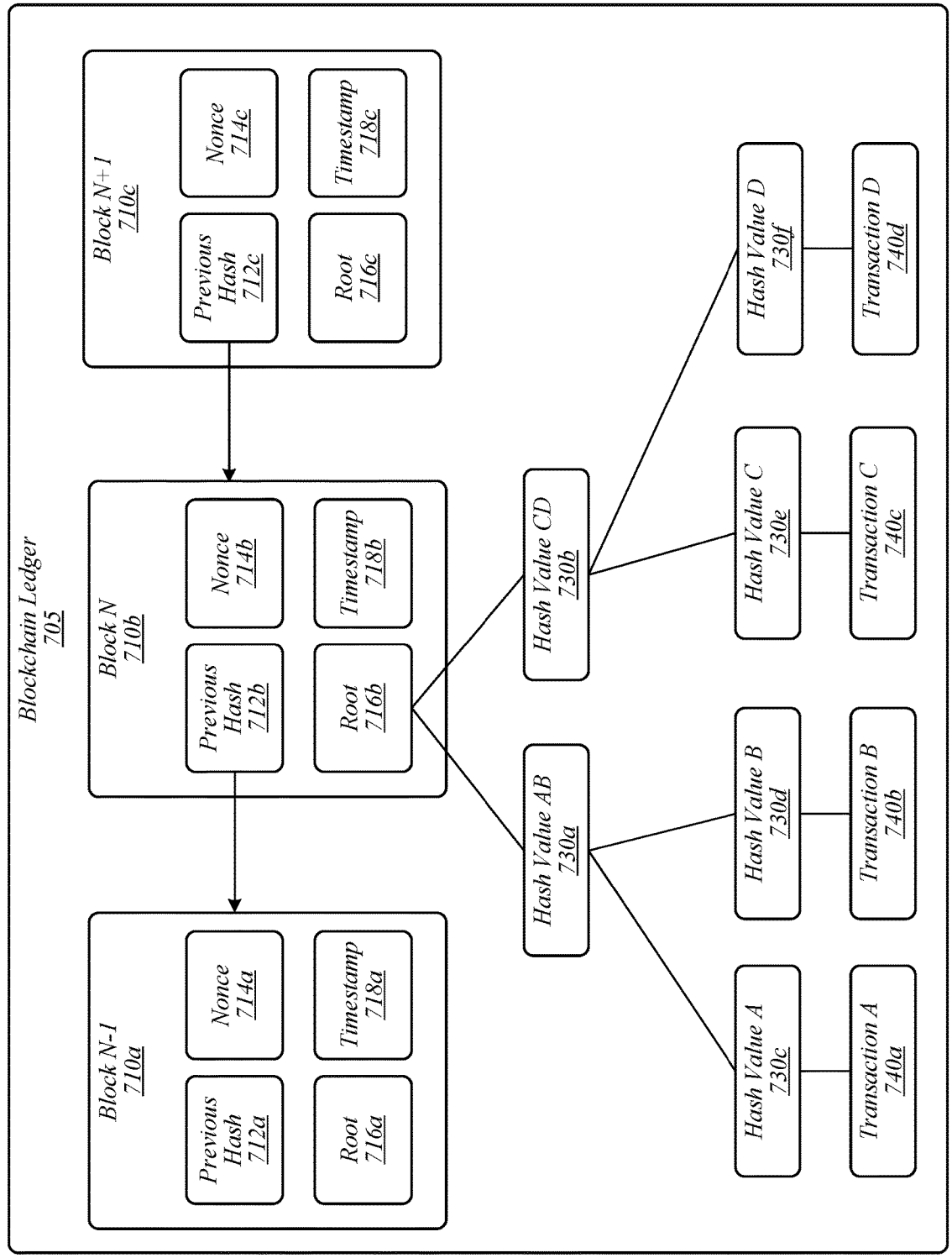
FIG. 7 depicts a blockchain ledger according to some embodiments.

FIG. 7 depicts an illustrative blockchain ledger 705 according to some embodiments. As shown in FIG. 7, blockchain ledger 705 may include a plurality of blocks 710a-c. Each of blocks 710a-c may include various block elements a previous has 712a-c that is a hash of the previous block, a nonce 714a-c, a root (or root hash) 716a-c, and a timestamp 718a-n. Blockchain ledger 705 according to some embodiments may include more or less block elements than the block elements depicted in FIG. 7. Embodiments are not limited in this context.

In the embodiment shown in FIG. 7, the root hash 716a-c may be associated with transactions 740a-d via a Merkel tree. Each of transaction 740a-d nodes are hashed into corresponding hash leaf nodes 730c-f, which are subsequently hashed to generate hash leaf nodes 730a and 730b. Root hash 716a-c is generated by hashing leaf nodes 730a and 730b. Various hashing cryptographic techniques may be used according to various embodiments, including, without limitation a SHA-2 cryptographic hash function, a SHA-256 cryptographic hash function, and/or the like. Embodiments are not limited in this context.

Figure 8:
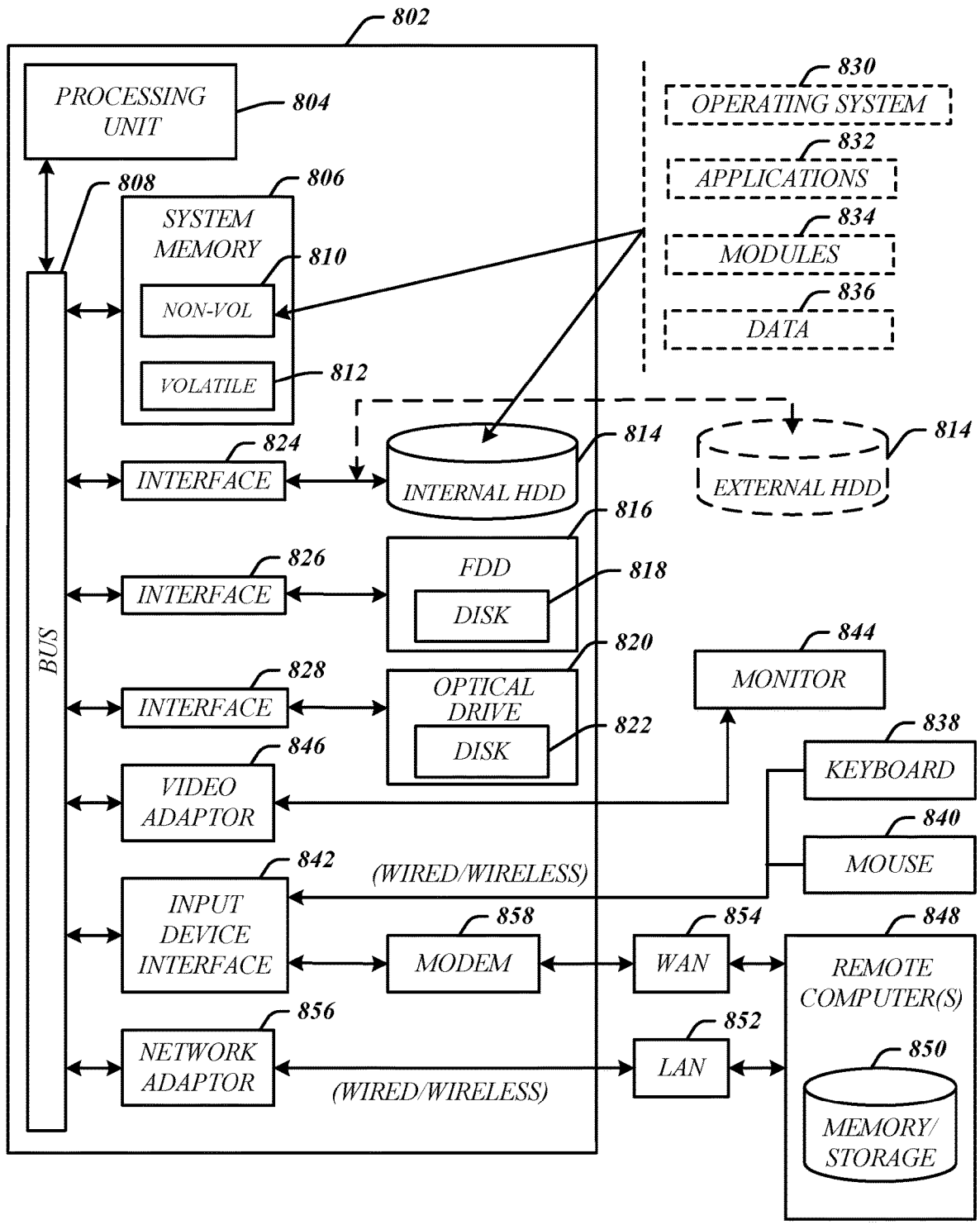
FIG. 8 illustrates an embodiment of a computing architecture.

FIG. 8 illustrates an embodiment of an exemplary computing architecture 800 suitable for implementing various embodiments as previously described. In various embodiments, the computing architecture 800 may comprise or be implemented as part of an electronic device. In some embodiments, the computing architecture 800 may be representative, for example, of apparatus 205, 305, and/or 405. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 800. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 800 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 800.

As shown in FIG. 8, the computing architecture 800 comprises a processing unit 804, a system memory 806 and a system bus 808. The processing unit 804 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 804.

The system bus 808 provides an interface for system components including, but not limited to, the system memory 806 to the processing unit 804. The system bus 808 can be any of several types of bus structure that may further interconnect to a memory bus (with or without a memory controller), a peripheral bus, and a local bus using any of a variety of commercially available bus architectures. Interface adapters may connect to the system bus 808 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 806 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 8, the system memory 806 can include non-volatile memory 810 and/or volatile memory 812. A basic input/output system (BIOS) can be stored in the non-volatile memory 810.

The computer 802 may include various types of computer-readable storage media in the form of one or more lower speed memory units, including an internal (or external) hard disk drive (HDD) 814, a magnetic floppy disk drive (FDD) 816 to read from or write to a removable magnetic disk 818, and an optical disk drive 820 to read from or write to a removable optical disk 822 (e.g., a CD-ROM or DVD). The HDD 814, FDD 816 and optical disk drive 820 can be connected to the system bus 808 by a HDD interface 824, an FDD interface 826 and an optical drive interface 828, respectively. The HDD interface 824 for external drive implementations can include at least one or both of Universal Serial Bus (USB) and IEEE 1384 interface technologies.

The drives and associated computer-readable media provide volatile and/or nonvolatile storage of data, data structures, computer-executable instructions, and so forth. For example, a number of program modules can be stored in the drives and memory units 810, 812, including an operating system 830, one or more application programs 832, other program modules 834, and program data 836. In one embodiment, the one or more application programs 832, other program modules 834, and program data 836 can include, for example, the various applications and/or components of apparatus 105, 205, 305, and/or 405.

A user can enter commands and information into the computer 802 through one or more wire/wireless input devices, for example, a keyboard 838 and a pointing device, such as a mouse 840. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 804 through an input device interface 842 that is coupled to the system bus 808, but can be connected by other interfaces such as a parallel port, IEEE 1394 serial port, a game port, a USB port, an IR interface, and so forth.

A monitor 844 or other type of display device is also connected to the system bus 808 via an interface, such as a video adaptor 846. The monitor 844 may be internal or external to the computer 802. In addition to the monitor 844, a computer typically includes other peripheral output devices, such as speakers, printers, and so forth.

The computer 802 may operate in a networked environment using logical connections via wire and/or wireless communications to one or more remote computers, such as a remote computer 848. The remote computer 848 can be a workstation, a server computer, a router, a personal computer, portable computer, microprocessor-based entertainment appliance, a peer device or other common network node, and typically includes many or all of the elements described relative to the computer 802, although, for purposes of brevity, only a memory/storage device 850 is illustrated. The logical connections depicted include wire/wireless connectivity to a local area network (LAN) 852 and/or larger networks, for example, a wide area network (WAN) 854. Such LAN and WAN networking environments are commonplace in offices and companies, and facilitate enterprise-wide computer networks, such as intranets, all of which may connect to a global communications network, for example, the Internet.

When used in a LAN networking environment, the computer 802 is connected to the LAN 852 through a wire and/or wireless communication network interface or adaptor 856. The adaptor 856 can facilitate wire and/or wireless communications to the LAN 852, which may also include a wireless access point disposed thereon for communicating with the wireless functionality of the adaptor 856.

When used in a WAN networking environment, the computer 802 can include a modem 858, or is connected to a communications server on the WAN 854, or has other means for establishing communications over the WAN 854, such as by way of the Internet. The modem 858, which can be internal or external and a wire and/or wireless device, connects to the system bus 808 via the input device interface 842. In a networked environment, program modules depicted relative to the computer 802, or portions thereof, can be stored in the remote memory/storage device 850. It will be appreciated that the network connections shown are exemplary and other means of establishing a communications link between the computers can be used.

The computer 802 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (e.g., electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. An apparatus, comprising:
a hardware processor; and
at least one memory storing logic comprising instructions configured to cause the hardware processor to:
receive analytical information from at least one analytical instrument, and
generate at least one record in a distributed ledger having a transaction associated with at least a portion of the analytical information, the analytical information comprising operating information for the analytical instrument, the operating information comprising one or more of an:
operating log comprising operating information associated with operation of the analytical instrument before, during, or after an analysis,
an audit trail configured to record information pertaining to compliance with a regulatory protocol or chain of custody, or
a digital signature configured to record an identity of an operator performing a function on the analytical instrument,
receive a request for the at least one record in the distributed ledger from a third party through an analytical information exchange platform, and
provide the at least one record in the distributed ledger to the third party in response to the request.

2. The apparatus of claim 1, the analytical information comprising analysis information, the analysis information comprising at least one of a spectrum or a chromatogram.

3. The apparatus of claim 1, the logic to determine compliance with a regulatory protocol based on at least one record of the distributed ledger.

4. The apparatus of claim 1, the logic to generate the record as part of an audit trail based on the analytical information within the distributed ledger.

5. The apparatus of claim 1, the logic to generate the record as part of a chain of custody based on the analytical information within the distributed ledger.

6. The apparatus of claim 1, the logic to implement a smart contract based on the analytical information via at least one record of the distributed ledger.

7. The apparatus of claim 1, the logic to verify at least a portion of the analytical information.

8. The apparatus of claim 1, the logic to generate the record in the distributed ledger responsive to a failure to verify the at least a portion of the analytical information.

9. The apparatus of claim 1, the logic to compare first analytical information associated with a first record in the distributed ledger with second analytical information associated with a second record in the distributed ledger to determine whether the first analytical information either matches or is determined to be substantially similar to the second analytical information.

10. The apparatus of claim 1, the analytical information comprising analysis information and operating information, the logic to retrieve at least one of analysis information or operating information from one or more records in one or more distributed ledgers based on criteria.

11. The apparatus of claim 10, the criteria comprising one or more of a designated time range, records created or that contain analytical information created by a particular analytical instrument, or records created by a particular entity.

12. The apparatus of claim 1, wherein the operating information comprises the operating log, the audit trail, and the digital signature.

13. The apparatus of claim 1, wherein the third party is a supplier of a product component, a manufacturer obtaining the product component from the supplier, a governmental or industry regulator, a healthcare entity, a research entity, or a certification entity.

14. The apparatus of claim 1, wherein the analytical information comprises an identifier, the identifier being a unique chemical or molecular fingerprint of a chemical compound analyzed to generate the analytical information, or a doping agent added to the chemical compound, wherein the identifier is provided as part of the record to the third party as an indication that a chain of custody for the chemical compound has been maintained.

15. The apparatus of claim 1, wherein the logic further comprises instructions for comparing the audit trail to expected historical or process information, determining that the audit trail does not match the historical or process information, and generating a record in the distributed ledger in response to the determining.

16. An analytical exchange system comprising:
   at least one computing device comprising:
   a hardware processor; and
   a non-transitory computer-readable medium storing logic to implement an analytical exchange platform, the logic comprising instructions configured to cause the hardware processor to:
     provide a distributed ledger,
     receive analytical information from at least one producer node for at least one analytical instrument,
     generate at least one record in the distributed ledger having a transaction associated with at least a portion of the analytical information, the analytical information comprising operating information for the analytical instrument, the operating information comprising one or more of an:
       operating log comprising operating information associated with operation of the analytical instrument before, during, or after an analysis,
       an audit trail configured to record information pertaining to compliance with a regulatory protocol or chain of custody, or
       a digital signature configured to record an identity of an operator performing a function on the analytical instrument,
     receive a request for the at least one record in the distributed ledger from a third party consumer node through an analytical information exchange platform, and
     provide the at least one record in the distributed ledger to the third party consumer node in response to the request.

17. The system of claim 16, the analytical information comprising analysis information, the analysis information comprising at least one of a spectrum or a chromatogram.

18. The system of claim 16, the logic to push a copy of a shared distributed ledger to that at least one consumer node.

19. The system of claim 16, the logic to determine compliance with a regulatory protocol based on at least one record of the distributed ledger.

20. The system of claim 16, the logic to generate the record as part of an audit trail based on the analytical information within the distributed ledger.

21. The system of claim 16, the logic to generate the record as part of a chain of custody based on the analytical information within the distributed ledger.

22. A computer-implemented method, comprising, by a processor:
   receiving analytical information from at least one analytical instrument; and
   generating at least one record in a distributed ledger having a transaction associated with at least a portion of the analytical information, the analytical information comprising operating information for the analytical instrument, the operating information comprising one or more of an:
     operating log comprising operating information associated with operation of the analytical instrument before, during, or after an analysis,
     an audit trail configured to record information pertaining to compliance with a regulatory protocol or chain of custody, or
     a digital signature configured to record an identity of an operator performing a function on the analytical instrument,
   receive a request for the at least one record in the distributed ledger from a third party through an analytical information exchange platform, and
   provide the at least one record in the distributed ledger to the third party in response to the request.

* * * * *